(12) United States Patent
Kato

(10) Patent No.: US 9,486,650 B2
(45) Date of Patent: Nov. 8, 2016

(54) PARTICLE BEAM THERAPY SYSTEM

(71) Applicant: MITSUBISHI ELECTRIC CORPORATION, Chiyoda-ku, Tokyo (JP)

(72) Inventor: Masayuki Kato, Tokyo (JP)

(73) Assignee: MITSUBISHI ELECTRIC CORPORATION, Chiyoda-Ku, Tokyo (JP)

(*) Notice: Subject to any disclaimer, the term of this patent is extended or adjusted under 35 U.S.C. 154(b) by 0 days.

(21) Appl. No.: 14/762,284

(22) PCT Filed: Apr. 19, 2013

(86) PCT No.: PCT/JP2013/061628
§ 371 (c)(1),
(2) Date: Jul. 21, 2015

(87) PCT Pub. No.: WO2014/171007
PCT Pub. Date: Oct. 23, 2014

(65) Prior Publication Data
US 2015/0352377 A1    Dec. 10, 2015

(51) Int. Cl.
*A61N 5/00* (2006.01)
*A61N 5/10* (2006.01)

(52) U.S. Cl.
CPC ..... *A61N 5/1075* (2013.01); *A61N 2005/1087* (2013.01); *A61N 2005/1088* (2013.01)

(58) Field of Classification Search
CPC .................. A61N 5/1075; A61N 2005/1088; A61N 2005/1087
USPC ............................................ 250/492.1–492.3
See application file for complete search history.

(56) References Cited

U.S. PATENT DOCUMENTS

2006/0102856 A1    5/2006  Matsuda et al.
2015/0126798 A1*   5/2015  Iwata ................... A61N 5/1043
                                                  600/1

FOREIGN PATENT DOCUMENTS

| JP | 2000-242722 A | 9/2000 | |
| JP | 2006-145213 A | 6/2006 | |
| JP | 2011-005096 A | 1/2011 | |
| JP | WO 2014030207 A1 * | 2/2014 | ........... A61N 5/1043 |

OTHER PUBLICATIONS

International Search Report (PCT/ISA/210) mailed on Jul. 16, 2013, by the Japanese Patent Office as the International Searching Authority for International Application No. PCT/JP2013/061628.

* cited by examiner

*Primary Examiner* — Michael Maskell
(74) *Attorney, Agent, or Firm* — Buchanan Ingersoll & Rooney PC

(57) ABSTRACT

Plural equipment control devices of a particle beam therapy system comprise an equipment operation parameter calculation unit calculating equipment operation parameters based on data given by equipment data servers individually and an equipment operation verification data generation unit generating equipment operation parameter verification data for verifying soundness of the equipment operation parameters, an equipment data server comprises an equipment operation parameter integrating calculation unit calculating so as to obtain equipment operation parameters of each equipment, an equipment operation parameter verification data integrating generation unit generating an equipment operation parameter verification data of each equipment for verifying soundness of equipment operation parameters of each equipment, and a verification data comparison unit comparing equipment operation parameter verification data of each equipment which is received from plural equipment control devices with equipment operation parameter verification data of each equipment which is generated by the operation parameter verification data integrating calculation unit.

4 Claims, 5 Drawing Sheets

| RECORD NO | KEY 1 BEAM CONDITION | KEY 2 EQUIPMENT CONTROL DEVICE IDENTIFIER | DATA 1 COMPUTATIONAL ALGORITHM DATA IDENTIFIER | DATA 2 EQUIPMENT OPERATION PARAMETER VERIFICATION DATA | DATA 3 VERIFIED FLAG |
|---|---|---|---|---|---|
| 1 | 400MeV/2.0nA | MAGNET001-I | ACC_ALGORYTHM20130205 | &1234ABCD | ON |
| 2 | 400MeV/2.0nA | MAGNET001-V | ACC_ALGORYTHM20130205 | &9876FEDC | ON |
| 3 | 400MeV/2.0nA | MAGNET002-I | ACC_ALGORYTHM20130205 | &10002000 | ON |
| 4 | 400MeV/2.0nA | MAGNET002-V | ACC_ALGORYTHM20130205 | &40008000 | ON |
| 5 | 380MeV/2.0nA | MAGNET001-I | ACC_ALGORYTHM20130206 | &234589AB | ON |
| 6 | 380MeV/2.0nA | MAGNET001-V | . | . | . |
| 7 | 380MeV/2.0nA | MAGNET002-I | ACC_ALGORYTHM20130206 | &01000200 | OFF |
| 8 | 380MeV/2.0nA | MAGNET002-V | ACC_ALGORYTHM20130206 | &00400060 | ON |

FIG. 2

PARTICLE BEAM THERAPY SYSTEM

TECHNICAL FIELD

This invention relates to a particle beam therapy system for performing therapy by irradiating an affected part such as a tumor with a particle beam.

BACKGROUND ART

Regarding radio-therapeutic apparatuses for cancer therapy, a cancer therapy device in which a proton, a heavy ion are used has been developed and constructed. As is well known, in comparison with conventional radiation therapy using X rays, gamma rays, etc., by performing therapy using a proton, a heavy ion, etc., an affected part of cancer can be intensively irradiated, therefore, therapy can be performed without affecting normal cells. Further, recently, advanced three-dimensional scanning methods such as a scanning irradiation method and stacked conformation radiotherapy method which can suppress the influence to normal cells are developed and practicalized. Advanced three-dimensional scanning methods perform more accurate dose distribution control by switching beam conditions finely while irradiation.

A particle beam therapy system comprises an irradiation system including a treatment room for irradiating predetermined particle beam to a patient according to a treatment plan, and an accelerator system in which a particle beam is generated according to a request for a particle beam in a treatment room and the generated beams are transported to a designated treatment room under predetermined beam conditions. Further, the accelerator system comprises an injector which generates a particle beam, a main accelerator including a synchrotron which accelerates a particle beam, a sub-system of high energy beam transport device including a rotating gantry which transports and distributes the accelerated high energy particle beam to a treatment room, and an accelerator control system. Each of the sub-systems further comprises equipment including electromagnets, a beam monitor, a high frequency accelerating cavity, etc. and the accelerator control system comprises an equipment control server, a data base, a client and an equipment control device which directly controls each equipment.

According to conventional particle beam therapy system, an equipment data server retains operation parameters of equipment which correspond to necessary beam conditions in the data base. Before starting treatment, operation parameters of equipment which conforms to necessary beam conditions is selected from the data base, the operation parameters which correspond to each equipment are downloaded in corresponding equipment control device in advance. During treatment, operation parameters which are necessary for designated beam condition are selected from operation parameters which are already downloaded by an equipment control device and equipment is controlled so as to supply a particle beam which conforms to the beam condition which is required. According to the above mentioned advanced three-dimensional scanning methods, it is necessary to supply particle beams having a plurality of beam conditions, in advance, therefore a plurality of equipment operation parameters are downloaded in an equipment control device. (for example, refer to Patent Document 1).

PRIOR ART REFERENCE

Patent Document

[Patent Document 1] Japanese Patent Application Laid-Open No. 2006-145213

DISCLOSURE OF THE INVENTION

Problems to be Solved by the Invention

Regarding conventional particle beam therapy system, it is configured such that the above-mentioned equipment data server obtains operation parameters of each equipment by performing calculation based on a necessary beam condition of a particle beam, before starting treatment, each of operation parameters of equipment corresponding to the necessary beam condition of a particle beam is downloaded in corresponding equipment control device. In general, an accelerator system comprises more than one hundred pieces of equipment, regarding pattern data which are parameters which change depending on time, generally, request for time resolution (clock) is 1 kHz or higher. Therefore, data size of operation parameters of all pieces of equipment corresponding to one beam condition is extremely large. For example, in a case where a number of pieces of equipment whose parameters change depending on time is fifty, an operation cycle of a synchrotron is five seconds, necessary clock is 10 KHz, as many as 250 thousand parameters are required. Consequently, it requires a long time to download operation parameters of equipment from an equipment data server to an equipment control device.

Further, in a case where during operation of particle beam therapy system, operation parameters of equipment which are downloaded into an equipment control device are lost or damaged, for some reasons, it requires to re-download the operation parameters of equipment from the equipment data server to the equipment control device. In the above-mentioned case, until re-downloading operation is completed, the accelerator system cannot supply an appropriate particle. Therefore, performing treatment should be stopped. As above-mentioned, according to conventional configurations, even when operation parameters of equipment are re-downloaded, it is required to be on standby for a long time, and restoration time from stopped state of a particle beam therapy system is prolonged. As a result, throughput of treatment may be degraded.

Further, when equipment is adjusted, there is a step such that while changing calculation conditions of operation parameters of each equipment, operation parameters by which desired beam condition can be obtained are determined for each equipment. In the above-mentioned step, every time when a calculation condition of operation parameters of each equipment is changed, it is required to download operation parameters of all pieces of equipment from an equipment data server to an equipment control device. Consequently, it requires a long time to adjust equipment.

In order to solve the above-mentioned problems, this invention is made. This invention aims to obtain a particle beam therapy system by which requiring time for downloading operation parameters of equipment is improved to be reduced, optimization of beam adjustment work and reduction of suspension time due to re-downloading of an equipment parameter can be realized.

Means for Solving the Problems

A particle beam therapy system according to this invention comprises an accelerator configured to accelerate a charged particle beam, a particle beam transport unit configured to transport a particle beam which is a charged particle beam which is generated by the accelerator, a particle beam irradiation unit configured to irradiate a particle beam which is transported by the particle beam transport unit to an irradiation objective, a plurality of equipment control devices which controls respectively a plurality of pieces of equipment which are provided at the accelerator, the particle beam transport unit and the particle beam irradiation unit and an equipment data server which gives data to the plurality of equipment control devices, wherein each of the plurality of equipment control devices comprises an equipment operation parameter calculation unit which performs calculation to obtain equipment operation parameters for operating an accelerator and transporting a particle beam by a particle beam transport unit based on data which is given by the equipment data server and an equipment operation parameter verification data generation unit which generates an equipment operation parameter verification data for verifying soundness of the equipment operation parameters which are obtained by calculating in the equipment operation parameter calculation unit; and the equipment data server comprises an equipment operation parameter integrating calculation unit which calculates so as to obtain each of equipment operation parameters for operating a plurality of devices based on data which is given to the plurality of equipment control devices, an equipment operation parameter verification data integrating generation unit which generates each of equipment operation parameter verification data for verifying soundness of each of equipment operation parameters which are obtained by calculating in the equipment operation parameter integrating calculation unit, and a verification data comparison unit which compares each of equipment operation parameter verification data which is received from a plurality of equipment control devices with each of equipment operation parameter verification data which is generated in the operation parameter verification data integrating generation unit.

Advantage of the Invention

According to a particle beam therapy system of this invention, it is configured not only for an equipment data server but also for an equipment control device to have a calculation facility of operation parameters of equipment corresponding to a beam condition, instead of downloading equipment operation parameters to an equipment control device, by downloading a necessary beam condition, the equipment can be controlled by operation parameters corresponding to the desired beam condition. In comparison with equipment operation parameters, data size of a beam condition is small, therefore, requiring time for downloading can be reduced, and even when many beam conditions are required, data size of a beam condition to be downloaded can be suppressed.

BRIEF DESCRIPTION OF THE DRAWINGS

FIG. 2 shows an example of data base which is stored in a data base of a particle beam therapy system according to Embodiment of this invention.

EMBODIMENTS FOR CARRYING OUT THE INVENTION

Embodiment 1

Figure 1:
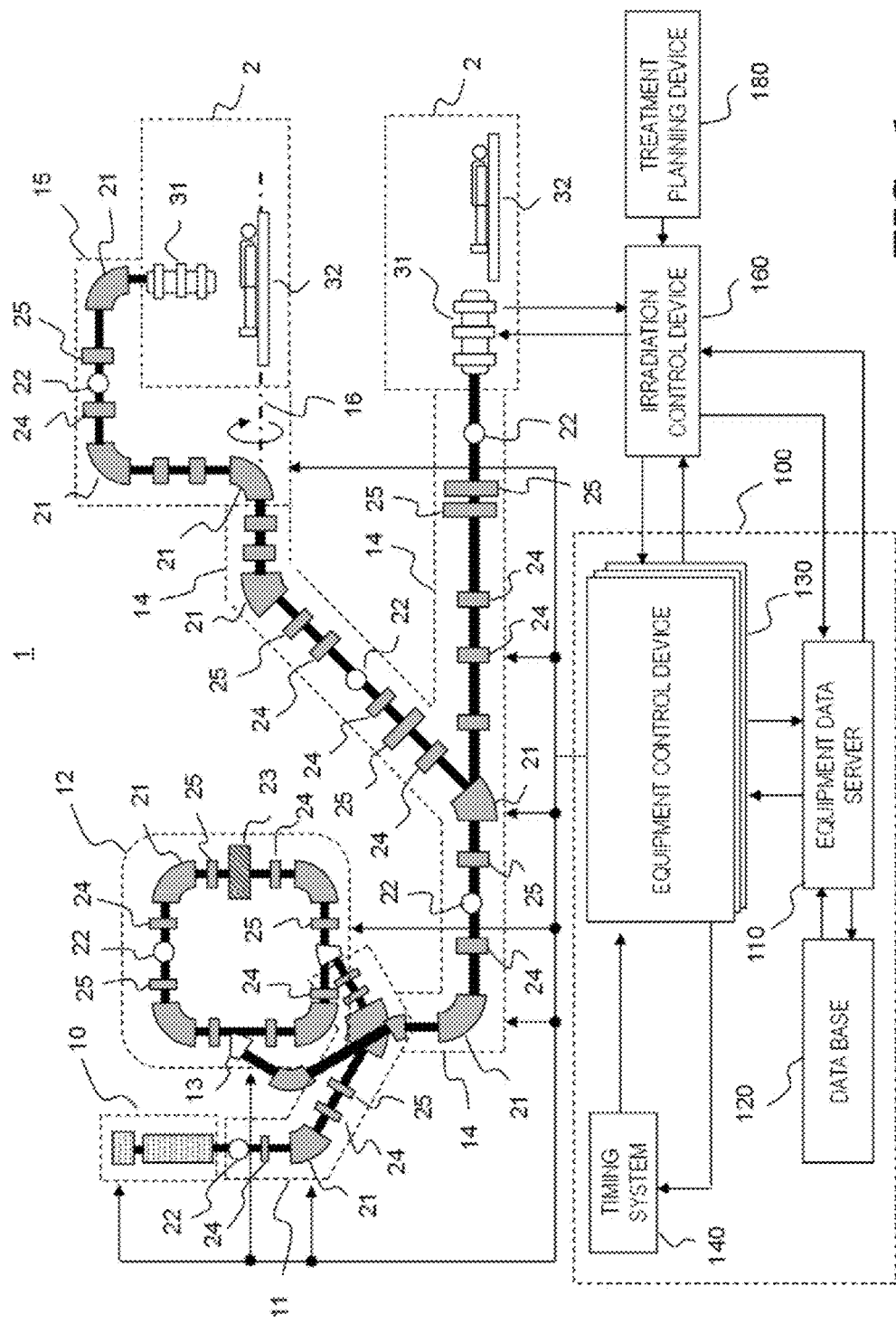
FIG. 1 is a block diagram showing the configuration of a particle beam therapy system according to Embodiment of this invention.

FIG. 1 is a block diagram showing the configuration of a particle beam therapy system according to Embodiment 1 of this invention. Hereinafter, Embodiment 1 of this invention will be described based on FIG. 1. An accelerator system 1 comprises a sub system including an injector 10, a low energy particle beam transport unit 11, a main accelerator 12, a beam extracting device 13, a high energy particle beam transport unit 14 and a rotating gantry 15 having a rotating axis 16, etc. Each of a sub system comprises bending electromagnets 21 for bending a travelling direction of a beam, a beam monitor 22, a high frequency accelerating cavity 23, electromagnets for correcting an orbit 24, quadrupole electromagnets for converging or diverging 25, etc. In a treatment room 2, a bed for a patient 32 and a particle beam irradiation unit 31 are provided.

Next, basic operation of the accelerator system 1 and the treatment room 2 will be described. In FIG. 1, a particle beam which is assemblage of ion (for example, a hydrogen ion, a carbon ion) which is generated at an ion source of the injector 10 is accelerated preliminarily by a pre-stage linear accelerator of the injector 10 so as to be accelerated to be predetermined kinetic energy. A particle beam which is accelerated preliminarily is transported from the injector 10, passed through the low energy particle beam transport unit 11 and guided to the main accelerator 12 (will be also simply referred to as an accelerator 12) while being subjected to bending, converging, diverging and correcting of orbit by various kinds of electromagnets 21, 24 and 25. In the main accelerator 12, various kinds of electromagnets including the bending electromagnets 21, the electromagnets for correcting an orbit 24 and the quadrupole electromagnets for converging or diverging 25 are set for a particle beam to circulate an orbit, and an accelerating electric field which is formed by the high frequency accelerating cavity 23 is repeatedly received. The particle beam is repeatedly accelerated by an accelerating electric field which is formed by the high frequency accelerating cavity 23, and its kinetic energy is increased together with acceleration. As kinetic energy is increased, magnetic field strength which is required for bending a particle beam is changed. Consequently, regarding equipment including various kinds of electromagnets 21, 24, 25 which compose the main accelerator 12, their operation parameters are changed depending on time. When a particle beam in the main accelerator 12 reaches predetermined kinetic energy and at the timing when the particle beam can be extracted, the particle beam is sent out to the high energy transport unit 14 (will be also simply referred to as a particle beam transport unit 14) by the beam extracting device 13.

A particle beam which is guided to the particle beam transport unit 14 is transported to an appropriate treatment room 2 by action of the bending electromagnets 21, etc. In a case where the particle beam transport unit 14 has the rotating gantry 15, the rotating gantry 15 is set by a predetermined angle so as to transport a particle beam. It is necessary to change the setting of operation parameters of each equipment such as the bending electromagnets 21 of the particle beam transport unit 14 in accordance with energy of a particle beam so as to transport the particle beam. Each sub system including the injector 10, the low energy particle beam transport unit 11, the main accelerator 12, the particle beam transport unit 14, the rotating gantry 15, etc. which compose the accelerator system 1 has the beam monitor 22, by using the beam monitors 22, the state of a particle beam is properly observed. The particle beam irradiation unit 31 which is provided in the treatment room 2 has a wobbler electromagnet or a scanning electromagnet, a scatterer, a ridge filter, a multi-leaf collimator, a bolus, etc. A particle beam which is transported to the treatment room 2 is irradiated so as to conform to a shape of an affected part of a patient who is secured to the bed for a patient 32 through the process of scanning to a direction which is perpendicular to a travelling axis of a particle beam, scattering, momentum dispersion, collimation, compensation, etc. and dose is given to the patient. An amount of a particle beam which is given to a patient is observed by a dose monitor which is contained in the particle beam irradiation unit 31, and a particle beam is irradiated until an amount of given dose reaches prescribed exposure value.

Particle beam irradiation is performed according to a treatment plan, and a treatment plan includes at least one beam condition of a particle beam, operation parameters setting of the particle beam irradiation unit 31 and an irradiation condition including an irradiation dose value. In some cases, one treatment plan includes a plurality of irradiation conditions and the irradiation conditions include two or more kinds of beam conditions. In the above-mentioned case, after the irradiation dose which is set to an irradiation condition corresponding to one beam condition is given, operation parameters of each equipment of the accelerator system 1 are changed so as to correspond to following beam condition, and irradiation is started under the following irradiation condition. Until the irradiation dose which is set by all irradiation conditions which are included in a treatment plan is given, the above-mentioned operation is repeated.

In the same way, the configuration of a control device which is provided in a particle beam therapy system according to the Embodiment will be described referring to FIG. 1. The accelerator system 1 is controlled by an accelerator control system 100. The accelerator control system 100 comprises an equipment data server 110, a data base 120, at least one equipment control device 130 and a timing system 140, and the equipment data server 110 and the equipment control device 130, and the equipment data server 110 and the data base 120 are connected individually by a network for various data communications. The equipment control device 130 and the timing system 140 are connected by a control signal line. Further, the equipment control device 130 is connected to a sub system or equipment by a signal line for setting and monitoring operation parameters of a sub-system (10 to 15) or that of equipment (21 to 25). The equipment control device 130 comprises a CPU for performing calculation processing, a memory which is a volatile data storage area where a CPU can access to the data at a high speed, and a disk which is nonvolatile data storage area, and each of them is connected by a communication bus in an equipment control device.

The treatment room 2 is controlled by an irradiation control device 160, the irradiation control device 160 is connected to a treatment planning device 180 and the equipment data server 110 by a network for data communication. Further, the irradiation control device 160, the equipment control device 130 and the particle beam irradiation unit 31 are connected by a signal line for setting and monitoring.

Next, a series of operations, from irradiation preparation to irradiation completion which are based on a treatment plan of a particle beam therapy system according to the Embodiment will be described referring to FIG. 1. A treatment planning device 180 transmits a treatment plan including an irradiation condition in a particle beam therapy system for a patient to the irradiation control device 160. When a treatment is given to a patient, the irradiation control device 160 reads out an irradiation condition which is included in a treatment plan corresponding to the patient, among the irradiation conditions, parameters regarding the particle beam irradiation unit 31 are set to the particle beam irradiation unit 31, at least one beam condition of a particle beam regarding the accelerator system 1 is transmitted to the equipment data server 110 as a beam condition setting. Instruction is given so as to be able to operate the accelerator system 1 under the beam condition.

The equipment data server 110 which receives a beam condition searches equipment operation parameters download state table of the data base 120 using at least one beam condition which is included in beam condition setting as a search key, and verifies such that the equipment operation parameters which conform to the beam condition are already set in the equipment control device 130. In a case where the equipment operation parameters are not correctly set in the equipment control device 130, the equipment data server 110 instructs the equipment control device 130 so as to set equipment operation parameters which conform to the beam condition, and verifies such that setting of the equipment control device 130 is completed. After it is verified, the equipment data server 110 transmits beam condition setting completion to the irradiation control device 160, and the accelerator system 1 informs such that preparation for operation corresponding to at least one beam condition of irradiation conditions which is included in the treatment plan is completed.

When a notice of setting completion of the beam condition is received, the irradiation control device 160 which completes setting irradiation parameters with regard to the particle beam irradiation unit 31 starts performing irradiation based on a treatment plan. First, the irradiation control device 160 outputs a beam condition request signal to the equipment control device 130. The signal includes a beam condition corresponding to a first irradiation condition of the treatment plan, the equipment control device 130 changes equipment operation parameters so as to correspond to the beam condition, by outputting setting completion signal, the completion of changing the equipment operation parameters are informed to the irradiation control device 160. At this timing, as it was described regarding an operation of the accelerator system 1, the accelerator system 1 is the state in which a particle beam of a beam condition corresponding to the beam condition request signal can be outputted, however, the beam extracting device 13 of the main accelerator 12 does not perform extracting a particle beam.

After the irradiation control device 160 verifies such that all of the equipment control devices 130 output a setting completion signal corresponding to a beam request signal with regard to a beam condition corresponding to a first irradiation condition, all of other preparation conditions with regard to an irradiation for a patient are completed, the irradiation control device 160 outputs a beam ON signal to the equipment control device 130. Each of the equipment control devices 130 which receives a beam ON signal performs setting each of equipment operation parameters with regard to each of the equipment so as for the beam extracting device 13 of the main accelerator 12 to perform extracting a particle beam and transporting the particle beam corresponding to the beam condition which is included in the beam condition request signal to a predetermined treatment room 2. The particle beam is processed to be a particle beam having a shape, etc. corresponding to the first irradiation condition by the particle beam irradiation unit 31, and is irradiated to the patient who is secured to the bed for a patient 32. While a beam ON signal is outputted, when a preparation condition regarding performing irradiation to the patient is not satisfied, for example, when an irradiation objective is not consistent with a particle beam due to respiration of the patient, the irradiation control device 160 temporarily stops a beam ON signal so as to stop extracting operation of the beam extracting device 13 of the accelerator system 1, and temporarily intercepts the irradiation of a particle beam. When a preparation condition regarding performing irradiation to the patient is satisfied again, the irradiation control device 160 outputs a beam ON signal so as to resume performing irradiation to a particle beam.

When a dose monitor which is included in the particle beam irradiation unit 31 monitors dosage which is given by the irradiation and detects such that the dosage reaches a prescribed exposure dose of the first irradiation condition, the irradiation control device 160 stops the beam ON signal, and the equipment control device 130 stops operation for extracting a particle beam by the beam extracting device 13 so as not to irradiate a particle beam under the first irradiation condition to a patient any more. In a case where a treatment plan includes only one irradiation condition, a treatment irradiation according to the treatment plan is completed. In a case where a treatment plan includes more than two irradiation conditions, the irradiation control device 160 repeats the above-mentioned procedure by using irradiation parameters setting corresponding to conditions which are subsequent to a second condition and a beam condition request signal, prescribed exposure dose is given under all irradiation conditions, and a treatment irradiation according to the treatment plan is completed.

Next, in the Embodiment of this invention, an operation of the equipment control device 130 which shows features of the invention, and cooperation with the equipment control device 130, the equipment data servers 110 and the data base 120 will be described in details.

Before performing a particle beam treatment by a particle beam therapy system, it is necessary for the accelerator system 1 to arrange a set of equipment operation parameters corresponding to a beam condition of an irradiation condition which is included in a treatment plan. Arranging the above-mentioned equipment operation parameters will be performed by the following procedure. First, equipment operation parameters corresponding to one beam condition are generated by predetermined means. The generated equipment operation parameters are adopted as operation parameters of the accelerator system 1 and a particle beam which is outputted from the accelerator system 1 is verified using the beam monitor 22. The above-mentioned series of work is repeated until a particle beam coincides with a desired beam condition, and equipment operation parameters which are obtained resultantly are registered in the data base 120. Alternatively, for example, in a case where environmental condition of the accelerator system 1 is changed, equipment operation parameters which are already registered are reviewed again, and are reregistered so as to be coincide with a desired beam condition. The above-mentioned provision work of equipment operation parameters is generally called a beam adjustment work. After a beam adjustment work is completed, the irradiation control device 160 transmits at least one beam condition request corresponding to a particle beam which is necessary for performing a treatment plan for a patient to the equipment data server 110 of the accelerator system 1, and gives an instruction to the accelerator system 1 to prepare to be able to operate under the beam condition corresponding to the treatment plan.

In the data base 120, a table, as shown in FIG. 2 for managing the state of equipment operation parameters which are set in the equipment control device 130 in the accelerator control system 100 is stored, and each record of the table has 'beam condition' and 'equipment control device identifier' as a search key, and 'computational algorithm data identifier', 'equipment operation parameter verification data' and 'verified flag' as a value.

Figure 3:
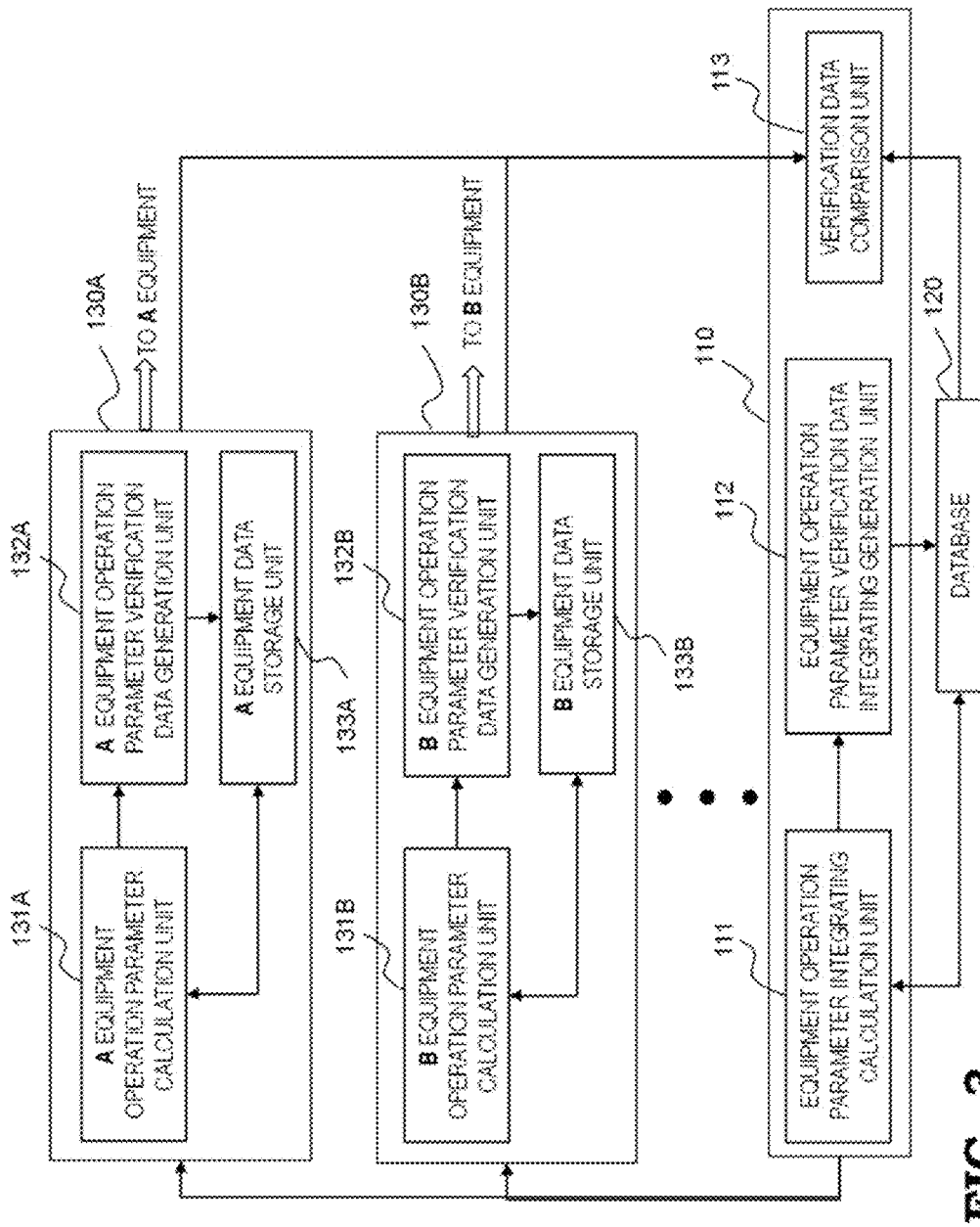
FIG. 3 is a block diagram showing the configuration of an equipment control device and an equipment data server of a particle beam therapy system according to Embodiment of this invention.

The equipment control device 130 and the equipment data server 110 have the configuration shown in FIG. 3. In FIG. 3, the equipment control device 130 for controlling each of a plurality of pieces of equipment is shown as A equipment control device 130A which controls A equipment, B equipment control device 130B which controls B equipment, etc. A equipment control device 130A comprises an A equipment operation parameter calculation unit 131A, an A equipment operation parameter verification data generation unit 132A, an A equipment data storage unit 133A, etc. Other equipment control devices have the similar configuration. An equipment operation parameter calculation unit of each equipment control device may be collectively referred as an equipment operation parameter calculation unit 131. In the same way, it may be referred as an equipment operation parameter verification data generation unit 132 and an equipment data storage unit 133.

On the other hand, the equipment data server 110 comprises an equipment operation parameter integrating calculation unit 111, an equipment operation parameter verification data integrating generation unit 112, a verification data comparison unit 113, etc.

Figure 4:
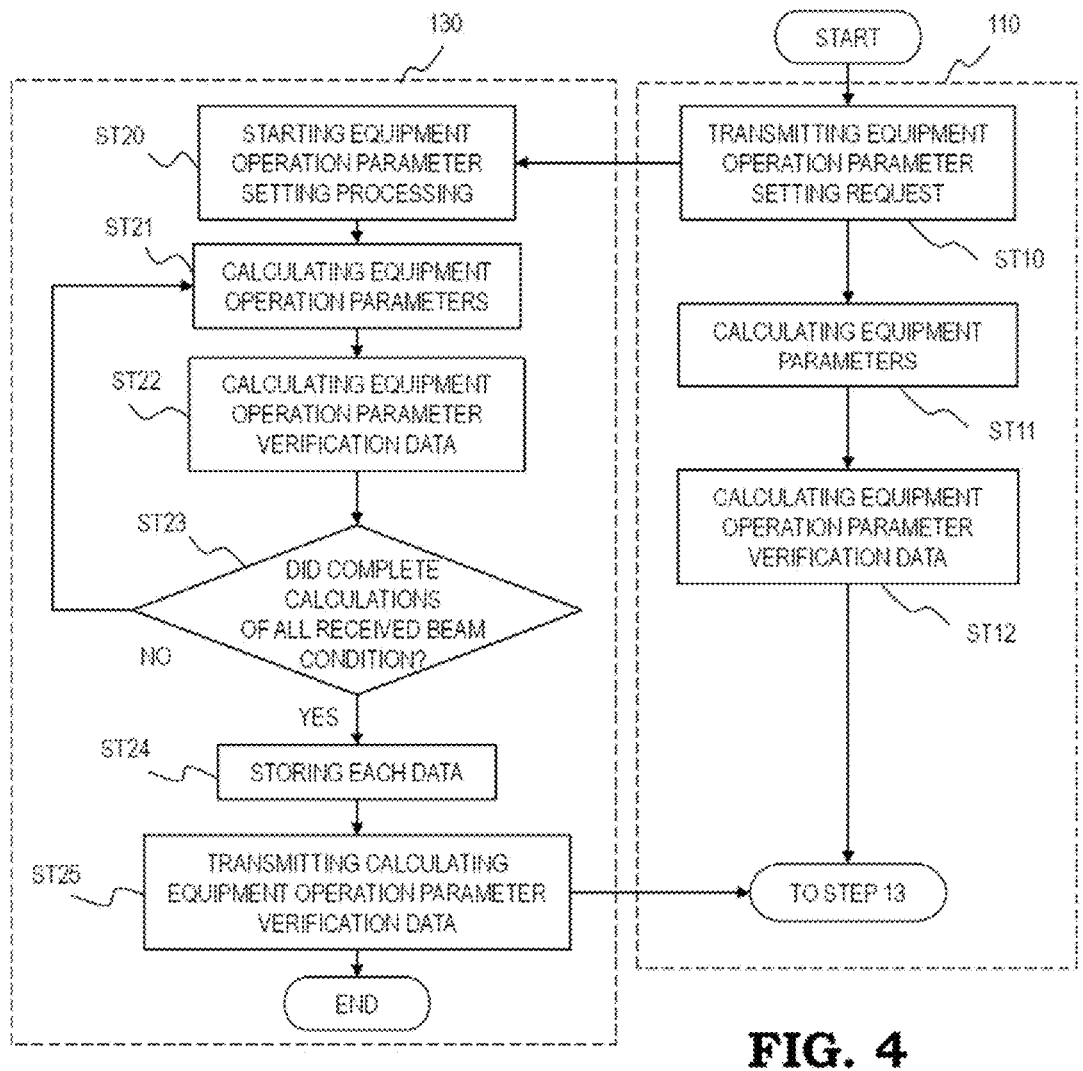
FIG. 4 is a flow chart showing the operation of a particle beam therapy system according to Embodiment of this invention.
Figure 5:
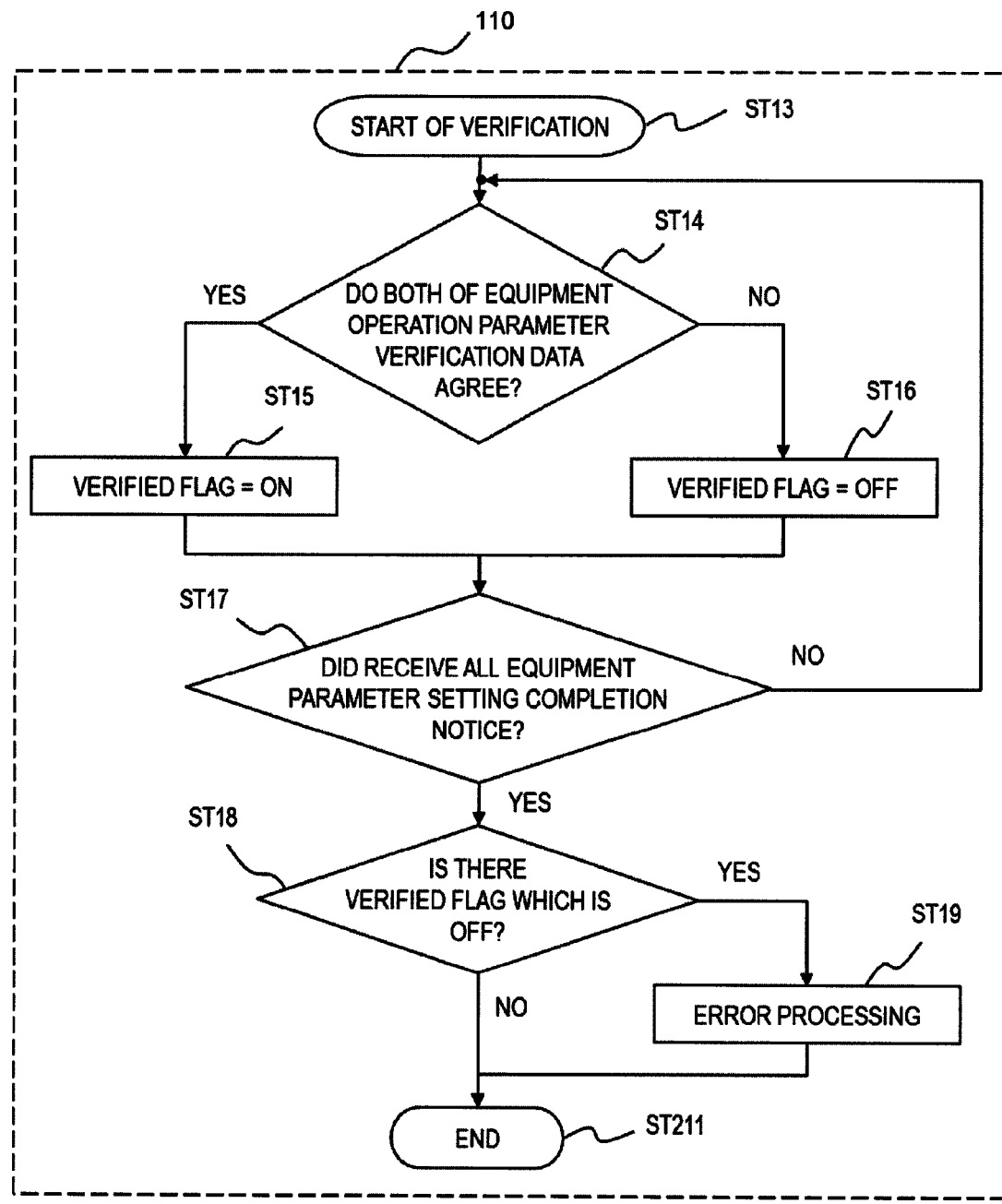
FIG. 5 is a flow chart showing the operation of a particle beam therapy system according to Embodiment of this invention following FIG. 4.

An operation of the accelerator control system 100 with regard to a beam adjustment work in the Embodiment of the present invention will be described below referring to flow charts in FIG. 4 and FIG. 5. The following procedure is a procedure in a case where it is necessary to create equipment operation parameters corresponding to a new beam condition in the accelerator system 1, or in a case where it is necessary to readjust equipment operation parameters corresponding to a beam condition which already exists in the accelerator system 1. First, the equipment data server 110 transmits an equipment operation parameter setting request including a beam condition data which includes at least one beam condition which is necessary to be generated or readjusted and calculation algorithm data which includes a part of or a whole of calculation algorithm which is necessary for calculating equipment operation parameters of the equipment to the equipment control device 130 which is necessary to be set (step ST10).

Calculation algorithm is algorithm for calculating equipment operation parameters of the equipment which are necessary for each equipment control device 130 which is composed of the accelerator control system 100 to make equipment which is to be controlled operate so as to correspond to a predetermined beam condition. Calculation algorithm may be, for example, a polynomial expression, and term number and a coefficient of each term may be data. As above mentioned, in advance, form of a plurality of formulas such as polynomial formulas is determined, a calculation algorithm data identifier may be given to each formula, and a calculation algorithm data identifier and coefficients which are included in the formula may be data of calculation algorithm. As above mentioned, instead of making whole of calculation algorithm to be data, by making form of polynomial formulas and coefficients which are included in the formula to be data, data volume can be farther reduced. A beam condition which is included in beam condition data includes, for example, a name of treatment room 2 to which a particle beam is transported, energy of a particle beam, strength of a particle beam, operation period, a beam diameter of a particle beam, gantry angle, etc. Further, calculation algorithm data can include, for example, a calculation program itself which can be performed by the equipment control device 130, individual features of equipment which are utilized by a calculation program which is incorporated in the equipment control device 130 and is to be controlled by the equipment control device 130, and a calculation parameter which does not depend on a beam condition of a particle beam which is outputted by the accelerator system 1 such as an operation clock of the timing system 140, etc.

When the equipment control device 130 receives an equipment operation parameter setting request from the equipment data server 110, the equipment operation parameter setting request is stored in the equipment data storage unit 133 and equipment operation parameter setting processing is started (Step ST20). The equipment operation parameter calculation unit 131 of the equipment control device 130 uses the beam condition data and the calculation algorithm data so as to calculate equipment operation parameters corresponding to at least one beam condition which is included in the beam condition data of equipment which is to be controlled by the equipment control device 130 (step ST21). Equipment operation parameters can include a current value and a voltage value of an electromagnet power supply, a frequency, a voltage and a phase of a high frequency which is supplied to a high frequency accelerating cavity, a setting value of equipment such as gantry angle, etc. and/or pattern data corresponding to a part of or a whole of operation period of the above-mentioned setting value, timing data regarding operation events of the accelerator system 1 including acceleration, extraction, deceleration, etc., a control parameter such as a feedback constant, correction coefficient, etc. and verity-data for verifying soundness of each data.

An equipment operation parameter verification data generation unit 132 of the equipment control device 130 calculates equipment operation parameter verification data whose data size is smaller than that of the equipment operation parameters and by which soundness of the equipment operation parameters can be verified later by using the equipment operation parameters (step ST22). As equipment operation parameter verification data, for example, checksum which is obtained as a result of exclusive operation of whole of equipment operation parameters, version of calculation algorithm data, data size of operation parameters or combination of the above mentioned may be used.

As the number of all beam conditions which are included in beam condition data which is received by the equipment control device 130, processing from the step ST21 to the step ST22 will be performed repeatedly (step ST23). The equipment control device 130 stores a beam condition which is included in beam condition data which is received in the step ST20 and all combinations of equipment operation parameters which are obtained in the step ST21 corresponding to the beam condition in the equipment data storage unit 133. Further, the equipment control device 130 stores the beam condition, the calculation algorithm data, the equipment operation parameters and equipment operation parameter verification data which is obtained in the step ST22 corresponding to the equipment operation parameter in the equipment data storage unit 133 (step ST24).

After the equipment control device 130 completes processing from steps ST21 to ST23 corresponding to all beam conditions which are included in the beam condition data, the equipment control device 130 transmits notice of equipment operation parameter setting completion to the equipment data server 110 (step ST25).

On the other hand, in an equipment operation parameter integrating calculation unit 111 of the equipment data server 110, after an equipment operation parameter setting request is transmitted to the equipment control device 130 in step ST10, by using beam condition data and calculation algorithm data which are included in the equipment operation parameter setting request, equipment operation parameters of equipment which are to be controlled by the equipment control device 130 corresponding to all beam conditions are calculated (step ST11). Further, in an equipment operation parameter verification data integrating generation unit 112 of the equipment data server 110, equipment operation parameter verification data corresponding to the equipment operation parameters which are obtained by calculation is calculated (step ST12). The data which is obtained by the above-mentioned calculation is stored in the database 120. As shown in FIG. 4, processing of steps ST11 to ST12 which is performed in the equipment data server 110 is performed independently of the processing of steps ST21 to ST23 which is performed by the equipment control device 130.

After the equipment data server 110 completes calculation processing of the step ST 12, when the equipment data server 110 receives equipment operation parameter setting completion from the equipment control device 130, in a verification data comparison unit 113, the equipment data server 110 starts a procedure of comparing equipment operation parameter verification data which is stored in the database 120 to equipment operation parameter verification data which is stored in the equipment data storage unit 133 of the equipment control device 130 (step ST13). As a result of comparison, in a case where both of them agree, the equipment data server 110 judges such that in the equipment data storage unit 133 of the equipment control device 130, intended equipment operation parameter are correctly stored (step ST14 YES), among tables of the database 120 shown in FIG. 2, the equipment data server 110 sets an equipment control device identifier corresponding to the equipment control device 130 and a value of 'verified flag' of record in which the beam condition is a key to be ON (step ST15). In a case where they do not agree, the equipment data server 110 judges such that intended equipment operation parameters are not correctly stored in a memory of the equipment control device 130, or inconsistency is generated in a beam condition or calculation algorithm data which is used for calculation (step ST14 NO), and the equipment data server 110 sets a value of 'verified flag' of the recorded to be OFF (step ST16).

When the equipment data server 110 receives all of equipment operation parameter setting completion notice from the equipment control device 130 which transmits an equipment operation parameter setting request, until 'verified flag' of corresponding record is set to be ON or OFF, processing of steps ST14, ST15 and ST16 is repeated (step ST17).

The equipment data server 110 searches a record of the database 120 using a beam condition which is included in beam condition data which is transmitted in the step ST10 as a key. In a case where at least one of values of 'verified flag' of all records corresponding to the search condition is OFF, the equipment data server 110 judges such that the accelerator control system 100 fails preparation for outputting a particle beam corresponding to the beam condition (step ST18 YES). In a case where the equipment data server 110 judges such that the preparation is failed, processing is returned to the processing of step ST 10 again, or error processing is performed such as displaying message for demanding to inquire the cause of error by outputting an error (step ST19), and processing is terminated (step ST211).

The equipment data server 110 searches a record of the database 120 using a beam condition which is included in a beam condition which is transmitted in step ST 10 as a key, in a case where values of 'verified flag' of all records corresponding to the search conditions are ON, the equipment data server 110 judges such that the accelerator control system 100 succeeds in preparing for outputting a particle beam corresponding to the beam condition (ST18 NO), and terminates processing (step 211).

According to the particle beam therapy system of the Embodiment of this invention having the above-mentioned configuration, following effects can be obtained. Conventionally, regarding equipment operation parameters for operating the accelerator system 1 under a specific beam condition, equipment operation parameters themselves are downloaded from a host computer having calculation power or storage power of the equipment operation parameters or a control device to a slave control device which actually performs equipment control (for example, refer to paragraph 0028 of Patent Document 1). Further, as above mentioned, generally, data size of equipment operation parameters including pattern data is extremely large, and further, one of the accelerator system 1 is composed of many pieces of equipment. Generally, there are a plurality of equipment control devices 130 which control the many pieces of equipment, therefore, data communication volume between the equipment data server 110 and all of the equipment control devices 130 is extremely large.

In the Embodiment of this invention, the equipment data server 110 and the data base 120 which correspond to a host computer transmit not equipment operation parameters themselves but calculation algorithm data and beam condition data which is used for obtaining equipment operation parameters to the equipment control device 130 which corresponds to a slave control device, and the equipment control device 130 obtains equipment operation parameters. In many cases, data size of calculation algorithm data and beam condition data is smaller than that of equipment operation parameters, in comparison with a case where conventional equipment operation parameters themselves are downloaded, while data communication volume is reduced, same effect as that of conventional equipment operation parameters download can be obtained. By reducing data communication volume, efficiency of beam adjustment work of a particle beam therapy system can be improved by shortening the communication time, by reducing necessary performance which is required for communication equipment, effect of cost suppressing of particle beam therapy system can be expected.

Further, by appropriately calculating equipment operation parameter verification data in each of equipment operation parameter verification data generation unit 132 based on equipment operation parameters which are stored in the equipment data storage unit 133 of each of the equipment control device 130, soundness, that is, whether deterioration or lacking of equipment operation parameters is generated or not can be verified. At this time, equipment operation parameter verification data is transmitted to the equipment data server 110 so as to compare to a value of equipment operation parameter verification data of a record which corresponds to the beam condition and an equipment control device identifier in the data base 120. Consequently, without transmitting equipment operation parameters themselves whose data size is larger than that of equipment operation parameter verification data, consistency between equipment operation parameters which are recognized by the data base 120 and equipment operation parameters which are stored in the equipment control device 130 can be verified.

Further, the equipment data storage unit 133 is composed of a disk which is a nonvolatile data storage region, and operation parameters which are calculated, operation verification data corresponding to the operation parameters, calculation algorithm data which is necessary for calculation and beam condition data are stored in the equipment data storage unit 133. Therefore, even in a case where data in a memory of the equipment control device 130 is lost due to loss of power, from the equipment data server 110, without downloading equipment operation parameters, equipment operation parameters corresponding to established beam condition can be automatically prepared. Further, by using equipment operation parameter verification data so as to verify equipment operation parameter verification data again, it can be checked such that equipment operation parameters are correctly reset. Consequently, without downloading data, similar result can be obtained, by omitting download time, recovery time from system stop state can be shortened, and as a result, effect of improving performance can be expected.

This invention is especially effective to a case of irradiation method so called a scanning irradiation method in which energy of a particle beam is changed for a plurality of times and is irradiated. According to the scanning irradiation method, a particle beam which is called a thin pencil beam is moved to a two-dimensional direction which is perpendicular to a travelling direction of the beam so as to form a two-dimensional irradiation distribution. Further, by energy of a particle beam, a position where absorbed dose of particle beam is a peak (referred as Bragg peak) is determined, therefore, by changing energy of a particle beam, an irradiation position in a beam travelling direction is changed. As above mentioned, according to a scanning irradiation method, by sequentially changing energy of a particle beam which is emitted from the accelerator 12 and sequentially forming a slice-state dose distribution in a depth direction, an irradiation field is formed by synthesized dose distribution.

In a scanning irradiation method, in order to change energy of a particle beam, it is necessary to change equipment operation parameters of each equipment which is composed of an accelerator system. Particularly, in order to obtain a particle beam having a predetermined energy, since equipment operation parameters of each equipment of the main accelerator 12 change depending on time, therefore, a large amount of equipment operation parameters are needed. As above mentioned, in performing beam adjusting work, in order to obtain a particle beam having a predetermined beam condition (for example, energy of a particle beam and a current value), it is necessary to set equipment operation parameters of each equipment by changing calculation algorithm, etc. for many times. In a scanning irradiation method, in many cases, a number of a predetermined beam condition is 10 or more, therefore, this invention can shorten communication time of data, beam adjustment work time can be reduced, and effect is especially large.

REMARKS

1: accelerator system
2: treatment room
12: main accelerator (accelerator)
14: high energy particle beam transport unit (particle beam transport unit)
21, 24, 25: electromagnet
31: particle beam irradiation unit
100: accelerator control system
110: equipment data server
111: equipment operation parameter integrating calculation unit
112: equipment operation parameter verification data integrating generation unit
113: verification data comparison unit
120: database
130: equipment control device
131: equipment operation parameter calculation unit
132: equipment operation parameter verification data generation unit
133: equipment data storage unit

The invention claimed is:

1. A particle beam therapy system comprising an accelerator configured to accelerate a charged particle beam,
a particle beam transport unit configured to transport a particle beam which is a charged particle beam generated by the accelerator,
a particle beam irradiation unit configured to irradiate a particle beam which is transported by the particle beam transport unit to an irradiation objective,
a plurality of equipment control devices which controls respectively a plurality of pieces of equipment which are provided at the accelerator, the particle beam transport unit and the particle beam irradiation unit and
an equipment data server which provides data to the plurality of equipment control devices,
wherein each of the plurality of equipment control devices includes
  (i) an equipment operation parameter calculation unit which performs calculation to obtain equipment operation parameters for operating the accelerator and transporting a particle beam by the particle beam transport unit based on data which is given by the equipment data server, and
  (ii) an equipment operation parameter verification data generation unit which generates equipment operation parameter verification data for verifying soundness of the equipment operation parameters which are obtained by calculating in the equipment operation parameter calculation unit; and
wherein the equipment data server includes
  (i) an equipment operation parameter integrating calculation unit which calculates so as to obtain each of equipment operation parameters for operating a plurality of devices based on data which is given to the plurality of equipment control devices,
  (ii) an equipment operation parameter verification data integrating generation unit which generates each of equipment operation parameter verification data for verifying soundness of each of equipment operation parameters which are obtained by calculating in the equipment operation parameter integrating calculation unit, and
  (iii) a verification data comparison unit which compares each of equipment operation parameter verification data which is received from a plurality of equipment control devices with each of equipment operation parameter verification data which is generated in the operation parameter verification data integrating generation unit.

2. The particle beam therapy system as claimed in claim 1 wherein the data which is provided to the equipment control device from the equipment data server includes calculation algorithm for calculation in the equipment operation parameter calculation unit.

3. The particle beam therapy system as claimed in claim 1 wherein the data which is provided to the equipment control device from the equipment data server includes a plurality of beam conditions corresponding to a plurality of energy of a particle beam for forming an irradiation field with integrated dose distribution by sequentially changing energy of a particle beam which is extracted from the accelerator so as to sequentially form a slice-state dose distribution in a depth direction in the irradiation objective.

4. The particle beam therapy system as claimed in claim 2 wherein the data which is provided to the equipment control device from the equipment data server includes a plurality of beam conditions corresponding to a plurality of energy of a particle beam for forming an irradiation field with integrated dose distribution by sequentially changing energy of a particle beam which is extracted from the accelerator so as to sequentially form a slice-state dose distribution in a depth direction in the irradiation objective.

* * * * *